United States Patent [19]

Chernin et al.

[11] Patent Number: 4,626,078
[45] Date of Patent: Dec. 2, 1986

[54] MULTIPLE PASS OPTICAL MATRIX SYSTEM

[75] Inventors: Semen M. Chernin, Moscow; Evgenia G. Barskaya, Leningrad, both of U.S.S.R.

[73] Assignee: Institut Khimicheskoi Fiziki, Moscow, U.S.S.R.

[21] Appl. No.: 761,587

[22] PCT Filed: Sep. 30, 1983

[86] PCT No.: PCT/SU83/00035
§ 371 Date: May 6, 1985
§ 102(e) Date: May 6, 1985

[87] PCT Pub. No.: WO85/01589
PCT Pub. Date: Apr. 11, 1985

[51] Int. Cl.[4] .................. G02B 17/06; G02B 5/10
[52] U.S. Cl. ................................. 350/504; 350/619
[58] Field of Search ............ 350/504, 619, 622, 623, 350/624; 356/246

[56] References Cited

U.S. PATENT DOCUMENTS 1,358,461 7/1920 Gilby et al. ........................ 101/19
3,825,325 7/1974 Hartley et al. .................... 350/619
4,209,232 6/1980 Chernin ............................. 350/619

FOREIGN PATENT DOCUMENTS 49183 4/1979 Japan ................................. 350/619
871125 10/1981 U.S.S.R.
1040454 9/1983 U.S.S.R.

OTHER PUBLICATIONS

Fujio Shimizu et al, "Stark Spectroscopy ...", Jour. of Applied Physics, vol. 46, No. 1, pp. 258, 259, Jan. 1975.
"Journal of the Optical Society of America," 66, No. 5, May 1976, John U. White, Very Long Optical Paths in Air, pp. 411–416.
P. L. Hanst, "Advances in Environmental Science and Technology," vol. II, ed. by J. N. Pitts and R. L. Metcalf, Wiley, NY, 1971, pp. 160–165.
"Applied Optics," vol. 10, No. 8, Aug. 1971, D. Horn and G. C. Pimentel, 2.5-km Low-Temperature Multiple-Reflection Cell, pp. 1892–1898.

Primary Examiner—Jon W. Henry
Attorney, Agent, or Firm—Lilling & Greenspan

[57] ABSTRACT

A multiple pass optical matrix system comprises two main and one additional objective mirrors arranged on a mount. The mount is mechanically connected with means for rotation of the mount about axes perpendicular and parallel to the image matrix row. The main and auxiliary field mirrors are placed opposite the mount along the longitudinal axis of the system.

4 Claims, 9 Drawing Figures

MULTIPLE PASS OPTICAL MATRIX SYSTEM

FIELD OF THE INVENTION

This invention relates to optical instruments and, in particular, to multiple pass optical matrix systems.

BACKGROUND OF THE INVENTION

All modern infrared spectrophotometers comprise optical multiple pass long-path systems. However, we are now witnessing the advent of new spectroscopy based on the use of high-intensity lasers and superhigh resolution laser semiconductor spectrometers. In these conditions, conventional multiple pass optical systems utilizing the classical White absorption cells are definitely obsolete since they cannot provide a large enough number of passes in the system.

Multiple pass optical systems showing great promise at the present stage of development are based on image matrices on arrays. But the existing matric systems are extremely complicated and unreliable.

Known in the art is a multiple pass optical matrix system (cf., for example, Journal of the Optical Society of America, 66, No. 5, May 1976, John U. White, Very Long Optical Paths in Air, pp. 411–416) comprising three objective mirrors arranged at the input and output of the laser beam, two main field mirrors having the radius of curvature equal to that of the objective mirrors and positioned at a distance equal to the radius of curvature of the latter, and also two diagonal mirrors having the total radius of curvature equal to the radius of curvature of an individual field mirror, arranged at an angle close to a right angle and adjoining one of the main field mirrors. In this system, each field mirror is individually mounted and can be rotated.

But this system is deficient in that the objective mirrors are individually mounted and rotated and the errors accumulate with the number of passes. The system, therefore, is extremely unstable, which is particularly felt if the number of passes is large.

Besides, the system comprises diagonal field mirrors operating at large incident angles, which results in greater astigmatism and, consequently, larger sizes of images.

One more deficiency consists in that the diagonal field mirrors produce additional reflecting surfaces impairing the translusency of the system.

This system is extremely complicated in design and adjustment, which affects its operational characteristics.

And, finally, the system can only operate with a coherent radiation source whose beam divergence is very small, which is a serious limitation to its application field.

Also known in the art is a multiple pass optical matrix system (cf., for example, P. L. Hanst, Advances in Environmental Science and Technology, vol. II, ed. by J. N. Pitts and R. L. Metcalf, Wiley, NY, 1971, pp. 160–165) comprising at least four objective mirrors, at least four field mirrors whose radii of curvature are equal to those of the objective mirrors, and which are arranged at a distance equal to the radius of curvature from said objective mirrors on the side of the entrance and exit apertures, and a means for coupling light beams out of the cell. In this system objective mirrors have individual adjustments, and one mirror can be rotated.

But this system is deficient in that individually adjustable objective mirrors and one angularly displacable mirror to change the number of passes can be the cause of error accumulation. The system is not vibration proof. The recommendation to cast the mirror array in epoxy cement produces a single purpose system which cannot be adjusted for any other application.

Besides, in this system each field mirror produces only one row of intermediate images, which is a limitation to the measuring range. To expand the measuring range by increasing the number of passes, more objective and field mirrors should be added, the total number of mirrors must be a multiple of four. Thus, a system for 220 passes and 10 rows of images in the matrix should have a total of 20 objective and field mirrors. The system becomes extremely complicated to operate and, consequently, unreliable.

Also known in the art is a multiple pass optical matrix system (cf., for example, U.S. Pat. No. 3,726,598, Cl. G OIJ 3.02, Apr. 10, 1973) wherein the radiation flux from an illumination source enters through an inlet window of the cell housing to hit one of the two rigidly secured main objective mirrors having the same radii of curvature and mechanically connected to a mount which is secured to a means for rotating said mirrors about an axis perpendicular to the row of images on the matrix, and further hits a main field mirror whose radius of cruvature is equal to that of the main objective mirror and which is arranged along the longitudinal axis of the system at a distance equal to the radius of curvature of the main objective mirrors, wherefrom the radiation flux is directed to another main objective mirror, is reflected therefrom to the main field mirror, and is once more directed to the first main objective mirror, and in the last pass leaves the system through the exit window.

This system is deficient in that the image matrix on the main field mirror has only two rows, thus limiting the number of passes and, therefore, the length of the optical path which can be achieved in this system.

SUMMARY OF THE INVENTION

This invention is to provide a multiple pass optical matrix system featuring such additional elements which make it possible to increase the number of intermediate images on the field mirror.

There is provided a multiple pass optical matrix system wherein the radiation flux from an illumination source comes through an entrance window of a housing and strikes one of the two rigidly secured main objective mirrors having the same radii of curvature, which are mechanically secured to a mount which is connected to a means for rotating said mirrors about an axis perpendicular to the row of images on an image matrix, and further falls on a main field mirror whose radius of curvature is equal to that of the main objective mirrors, which is arranged along the longitudinal axis of the system at a distance equal to the radius of curvature of the main objective mirrors and from which the radiation flux is directed to another main objective mirror, is reflected therefrom to the main field mirror, and from there is directed to the first main objective mirror, and, in the last pass, leaves the system through the exit window of the housing, and which, according to the invention, comprises an additional objective mirror having same radius of curvature, which is mechanically secured to the mount, a means for rotation about an axis parallel to the image matrix row, which is connected to the mount, and an auxiliary field mirror having the same radius of curvature, which is arranged on the same axis as the entrance and exit windows and close to the main field mirror.

Advisably, in the proposed matrix system, the mount should be made of two parts, one part carrying two main objective mirrors and connected to the means for rotation about an axis parallel to the image matrix row, and the other part carrying the additional field mirror.

Desirably, the proposed system should comprise one more additional objective mirror having the same radius of curvature, which is mechanically connected to the mount and rigidly secured to the additional objective mirror, the center of curvature of the main field mirror being positioned in the center of symmetry of the main and additional objective mirrors, while the center of curvature of the auxiliary field mirror is located in the center of symmetry between the first main objective mirror and respective additional objective mirrors.

Preferably, in the proposed matrix system, the mount should be made as a plate whereon the main and additional objective mirrors are installed.

This invention permits a substantial increase in the number of rows in the image matrix and, consequently, makes the optical path much longer.

In addition, this invention makes it possible to obtain a double superposition of images in the matrix, which can also increase the optical path.

BRIEF DESCRIPTION OF DRAWINGS

The invention will now be described in more detail with reference to specific embodiments thereof and to the accompanying drawings, wherein.

DETAILED DESCRIPTION OF THE INVENTION

Figure 1:
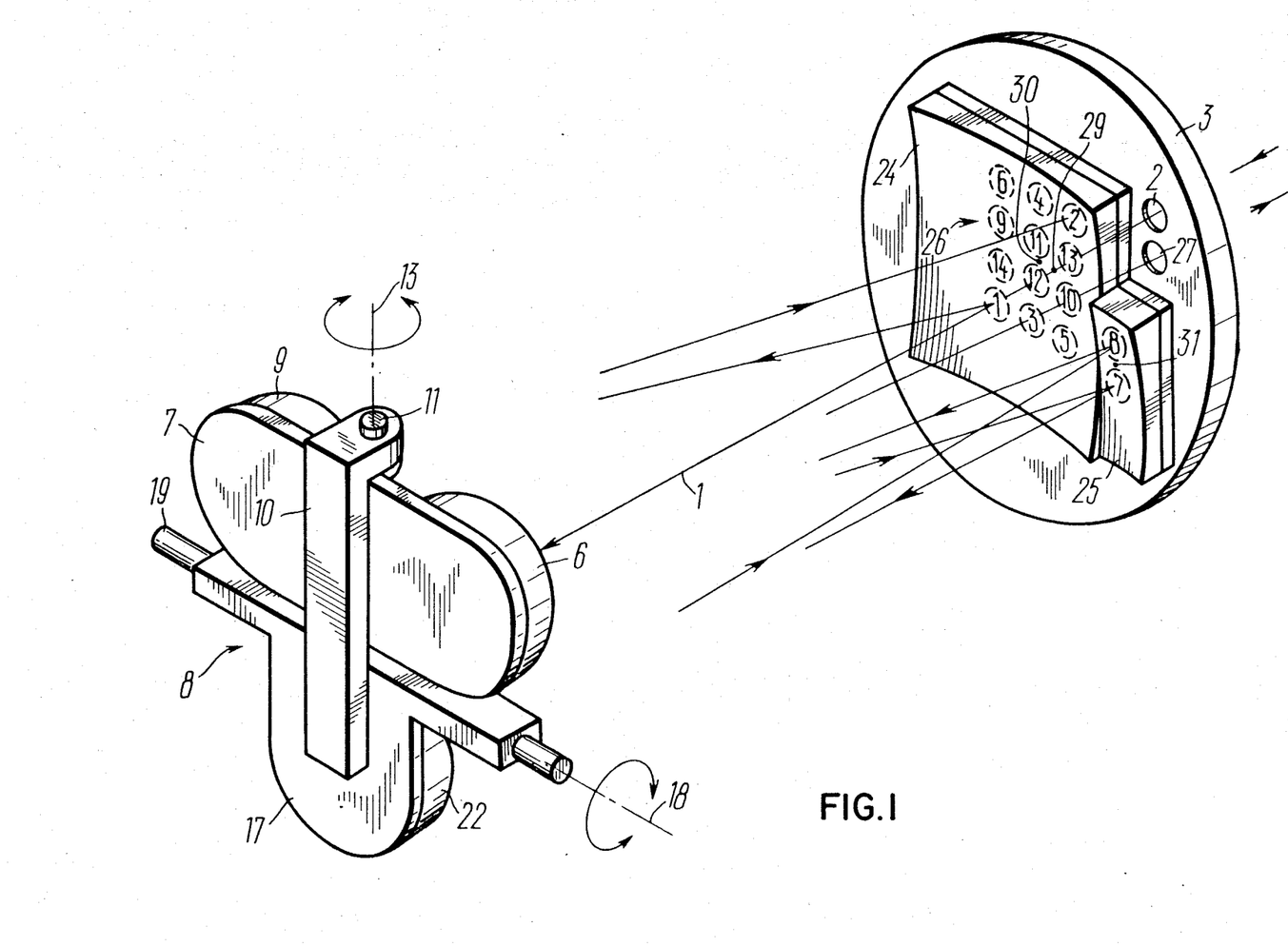
FIG. 1 shows a perspective view of a multiple pass optical matrix system featuring three objective mirrors, according to the invention.
Figure 2:
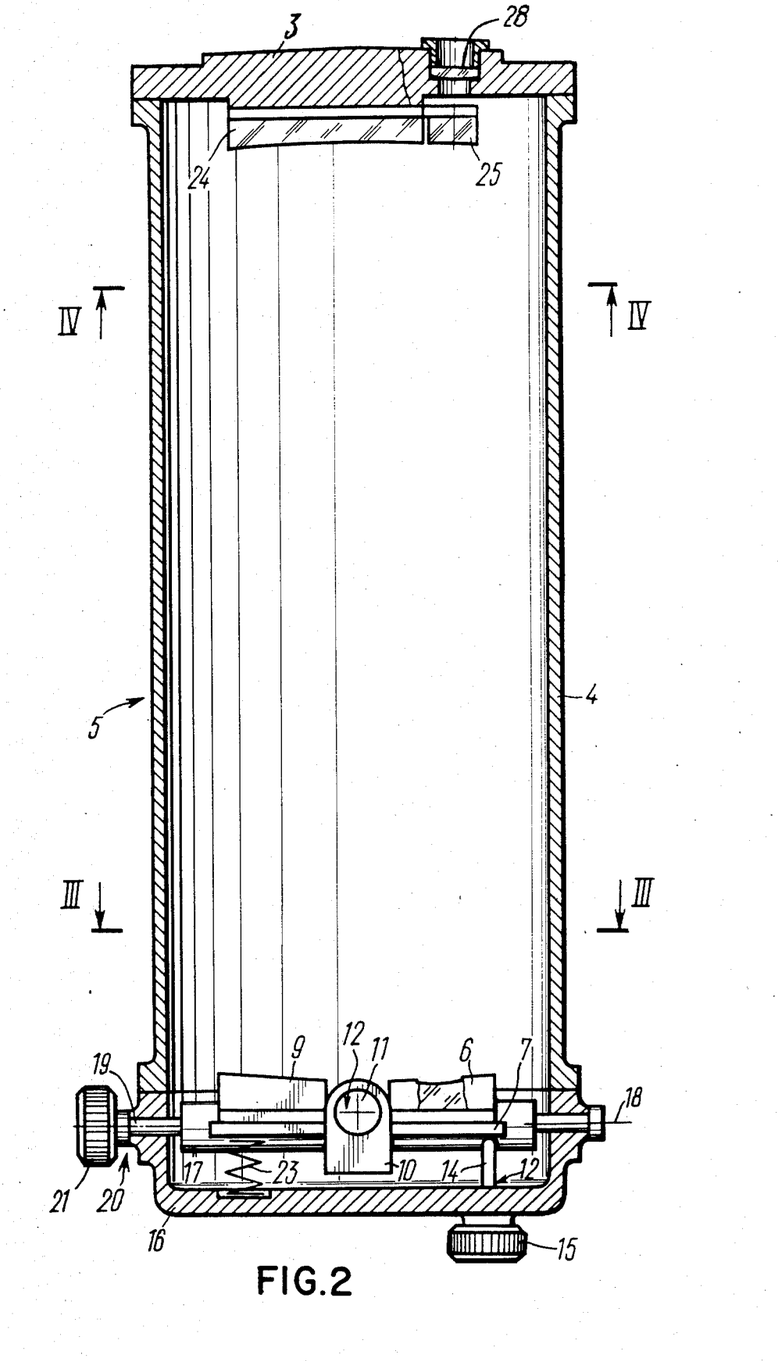
FIG. 2 shows a longitudinal sectional view of an absorption cell containg the multiple optical matrix system of FIG. 1, according to the invention.
Figure 3:
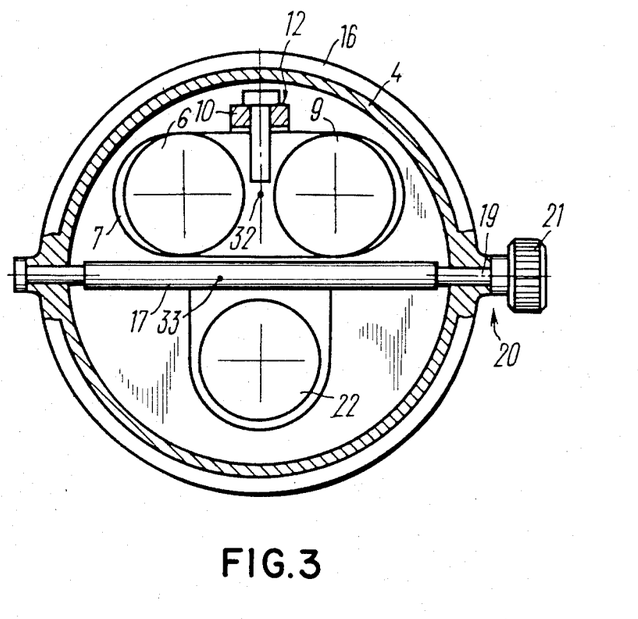
FIG. 3 shows a cross sectional view taken along line III—III of FIG. 2 and turned by 180°, according to the invention.

In a multiple pass optical matrix system according to the invention a radiation flux 1 (FIG. 1) from a radiation source (not shown) is supplied through an entrance opening 2 made in a lid 3 of a housing 4 (FIG. 2) of a cell 5, and falls on a main objective mirror 6 (FIGS. 1, 2, 3). The objective mirror 6 is placed in the path of the flux 1 on a plate 7 of a mount 8. A main objective mirror 9 is located on the plate 7 next to the objective mirror 6. The plate 7 is connected to a shaped strip 10 by a pivot shaft (rod 11) of a means 12 for rotation of the plate 7 about an axis 13. The means 12 also comprises a screw 14 with a hand nut 15. The screw 14 extends through a cover 16 of the housing 4 and butts up against the plate 7. The strip 10 is secured to a cross-piece 17 of the mount 8, which can be tilted in relation to a horizontal axis 18 on a support shaft (support roller 19) of a means 20 for rotation about the axis 18, which extends through the base of the cross-piece 17 and openings in the housing 4. The means 20 also comprises a hand nut 21 secured to the roller 19. An additional objective mirror 22 is installed on the cross-piece 17. A spring 23 is inserted between the plate 7 and the cover 16. A main field mirror 24 (FIGS. 1, 2 and 4) is placed in the path of the flux 1 reflected from the objective mirror 6. Beneath the entrance opening 2 and next to the field mirror 24 is placed an auxiliary field mirror 25. All objective mirrors 6,9,22 and field mirrors 24 and 25 have the same radius of curvature. Digits from 1 to 14 on the field mirrors 24 and 25 are to indicate the sequence of images forming a rectangular image matrix 26 whose rows are perpendicular to the axis 13 and parallel to the axis 18. An exit opening 27 is provided in the cover 3 on the vertical axis of the entrance opening 2 and above the field mirror 25 for the radiation flux 1 to leave the system in the last pass. The openings 2 and 27 are provided with windows 28 transparent to the radiation flux 1. The centers of curvature of the objective mirrors 6 and 9 are indicated by respective points 28 and 30 on the field mirror 24, and of the objective mirror 22 by a point 31 on the field mirror 25. The center of curvature of the field mirror 24 is located in the center of symmetry of the objective mirrors 6 and 9 and is indicated by a point 32. The center of curvature of the field mirror 25 is indicated by a point 33.

In an alternative embodiment of a multiple pass optical matrix system, a mount 34 (FIG. 5) comprises a plate 35 (FIGS. 5 and 6) and a ring 36 connected by a pivot shaft (pins 37) of the means 12. The ring 36 is secured to a support shaft (pins 38) of the means 20. Pins 38 extend through holes in the housing 4. Mounted on the plate 35 are two main objective mirrors 39 and 40 and two additional objective mirrors 41 and 42. A plate spring 43 is inserted between the plate 35 and cover 16. The center of curvature of the main field mirror 24 is located in the center of symmetry of the objective mirrors 39,40,41 and 42, and is indicated by a point 44. The center of curvature of the auxiliary field mirror 25 is located between the objective mirrors 39 and 41, in their center of symmetry and indicated by a point 45. The objective mirrors 39,40, 41 and 42 and field mirrors 24 and 25 have the same radius of curvature.

Figure 7:
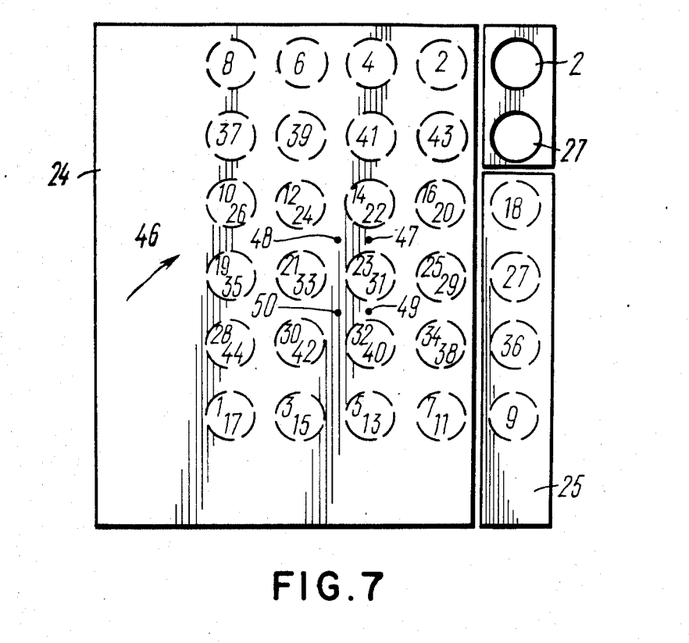
FIG. 7 shows a view taken along arrow A of FIG. 5, the main and additional field mirrors being enlarged, according to the invention.

Referring to FIG. 7, a rectangular image matrix 46 is provided for 90 passes of the radiation flux 1, the sequence of images being indicated by digits from 1 to 44. The matrix rows are perpendicular to the axis 13 and parallel to the axis 18. The centers of curvature of the pairs of objective mirrors 39,40 and 41, 42 are located on the surface of the field mirror 24 and indicated, respectively, by points 47, 48, 49 and 50.

Figure 8:
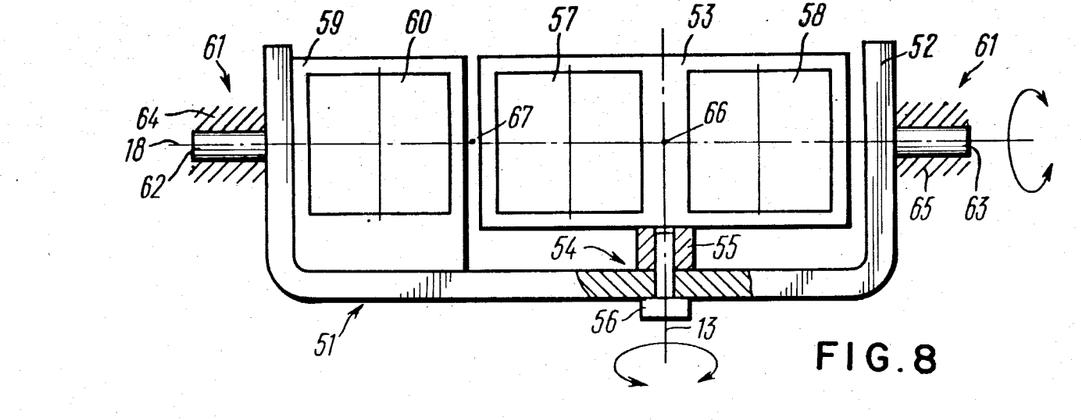
FIG. 8 shows a schematic view of a mount and three square objective mirrors arranged in a row, according to the invention.

In one more embodiment of a multiple pass optical matrix system, a mount 51 (FIG. 8) comprises a bracket 52 with a plate 53 being placed inside said bracket 52. A means 54 for rotation about the axis 13 comprises a sleeve 55 and a pin 56 extending through a hole in the bracket 52, and the sleeve 55. The plate 53 is fit on the pin 56. Main rectangular objective mirrors 57 and 58 are located on the plate 53. A cheek-piece 59 is secured to the face of the bracket 52 to carry an additional rectangular objective mirror 60. The objective mirrors 57, 58 and 60 are arranged in one line on the horizontal axis 18. A means 61 for rotation about the axis 18 comprises pins 62 and 63 secured to the bracket 52 and placed in sleeves 64 and 65 repectively. The center of curvature of the field mirror 24 (FIG. 1) is situated in the center of symmetry of objective mirrors 57 and 58 and designated by a point 66 (FIG. 8). The center of curvature of the field mirror 25 (FIG. 1) is located between the objective mirrors 57 and 60 (FIG. 8) and designated by a point 67.

And, finally, in still another embodiment of a multiple pass optical matrix system, a mount 68 (FIG. 9) comprises a bracket 69 and sleeves 70 and 71 made integral therewith. A plate 72 is located inside the bracket 69 and carries two main rectangular objective mirrors 73 and 74 and two additional rectangular objective mirrors 75 and 76 arranged in one row along the horizontal axis 18. The pin 56 with the sleeve 55 of the means 54 is secured to the bracket 69. The pins 62 and 63 are located, respectively, in the sleeves 70 and 71. The center of curvature of the field mirror 24 (FIG. 7) is located in the center of symmetry of the objective mirrors 73, 74 and 75, 76 (FIG. 9) and designated by a point 77. The center of curvature of the field mirror 25 (FIG. 1) is located in the center of symmetry of the objective mirrors 73 and 75 and designated by a point 78.

A multiple pass optical matrix system of FIGS. 1, 2, 3 and 4 operates as follows.

The radiation flux 1 passes through the entrance opening 2 and falls on the main objective mirror 6 which produces the first intermediate image of the entrance opening 2 on the surface of the field mirror 24 (digit 1 encircled by a dotted line). The plate 7 of the mount 8 and, therefore, the objective mirrors 6 and 9 can be turned by the hand nuts 15 and 21, respectively, of the means 12 and rotated about the axis 13 perpendicular to the rows of the image matrix 26; the means 20 for rotating the plate 7 about the axis 18 parallel to the rows of the image matrix 26. The tilting angle of the objective mirrors 6 and 9 dictates the distance from the entrance opening 2 to its first image in the horizontal row of the image matrix 26 on the main field mirror 24 (digit 1 encircled by a dotted line). The tilt of the mount 8 together with the objective mirrors 6,9 and 22 dictates the downward vertical displacement of the image. After the first image is formed, the radiation flux is reflected from the field mirror 24 to the objective mirror 9 which produces a second image (digit 2 encircled by a dotted line). The main objective mirrors 6 and 9 alternately focus the images of the entrance opening 2 on the field mirror 24 with a certain displacement until two rows of images are formed (digits 6,4,2 encircled by dotted lines form the first row, while digits 1,3,5—the second row) and the image finds itself on the field mirror 25 (digit 7 encircled by a dotted line). The radiation flux reflected from the field mirror 25 falls on the objective mirror 22 which returns it to the field mirror 25 with a vertical displacement. The radiation flux 1 is further directed to the objective mirror 6 and a next pair of rows is formed as described above in the image matrix 26 and so on until the last image comes to the exit opening 27.

During the simultaneous rotation of the objective mirrors 6 and 9, their centers of curvature (points 29 and 30) slide over the surface of the field mirror 24, the distance between them remains unchanged. When the mount 8 is tilted, the objective mirrors 6 and 9 are displaced vertically. The vertical interval between the line along which the centers of curvature (points 29 and 30) of the objective mirrors 6 and 9 situated and the center of curvature (point 31) of the objective mirror 22 remains permanent. Consequently, the number of passes of the radiation flux 1 can be changed.

The adjustable number of passes of the flux 1 through the system of three objective mirrors 6, 9, and 22 produces series of numbers satisfying specific relations depending on the number of rows and columns in the matrix 26. The number of passes of the flux 1 can be obtained from the following relation:

$$N = 2mn - 2,$$

where
N is the number of passes
m is the number of rows making up a series of natural numbers 2,4,6,8,10 . . . ;
n is the number of columns making up a series of natural numbers 1,2,3,4,5 . . .

Figure 4:
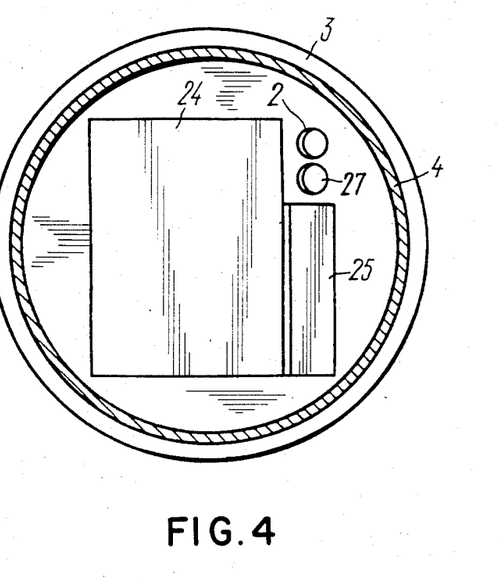
FIG. 4 shows a cross sectional view taken along line IV—IV of FIG. 2, according to the invention.
Figure 5:
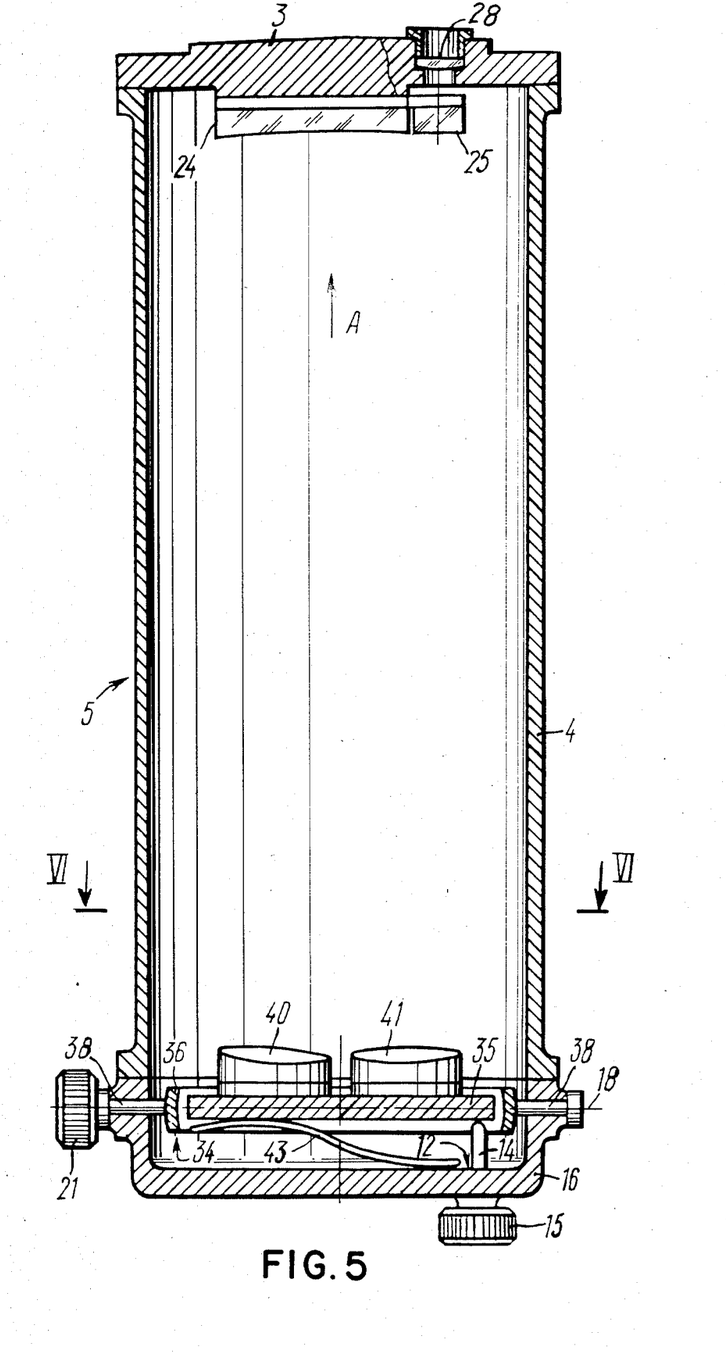
FIG. 5 shows a longitudinal sectional view of an absorption cell containing a multiple pass optical matrix system having four objective mirrors, according to the invention.
Figure 6:
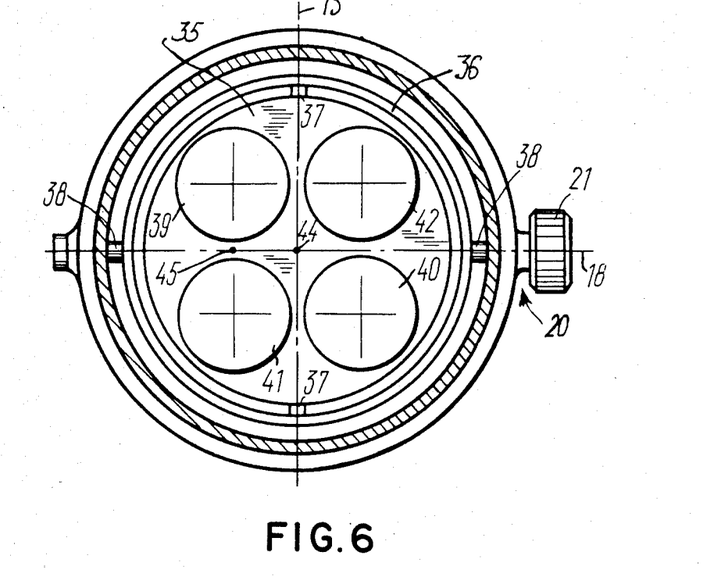
FIG. 6 shows a cross sectional view taken along line VI—VI of FIG. 5 and turned by 180°, according to the invention.

A multiple pass optical matrix system of FIGS. 4,5 and 7 operates as follows.

The radiation flux 1, similarly to the above embodiment, passes through the entrance opening 2 to fall onto the objective 39 which produces a first intermediate image of the entrance opening 2 on the surface of the field mirror 24 (digit 1 and digit 17 encircled together by a dotted line). The hand nut 15 of the means 12 is used to turn the plate 35 of the mount 34 together with the main objective mirrors 39 and 40 and additional objective mirrors 41 and 42. The plate 35 is turned about the axis 18 parallel to the rows of the image matrix 46 by the hand nut 21 of the means 20. The fixed turn of the plate 35 determines the distance from the entrance opening 2 to its first image in the horizontal row of the image matrix 46 on the field mirror 24. The fixed tilt of the plate 35 determines the downward vertical displacement of this image. After the first image is formed, the flux 1 is reflected from the field mirror 24 to the objective mirror 40 which produces a second image (digit 2 encircled by a dotted line). The objective mirrors 39 and 40 alternately focus the image of the entrance opening 2 on the field mirror 24 with a certain displacement until two rows of images (digits 8,6,4,2 encircled by dotted lines form the first row, and digits 1,3, 5,7 encircled by dotted lines for the second row) are formed and the last image finds itself on the auxiliary field mirror 25 (digit 9 encircled by a dotted line). The radiation flux 1 reflected from the field mirror 25 is directed to the objective mirror 41. The objective mirrors 41 and 42 alternately focus images and produce two new rows of images on the field mirror 24, and the last image is again on the field mirror 25 (digit 18 encircled by a dotted line). Then the objective mirrors 39 and 40 are again engaged. This goes on until the last image comes to the exit opening 27.

When the plate 35 turns, the centers of curvature (points 47,48,49,50) of the objective mirrors 39, 40,41 and 42 slide over the surface of the field mirror 24, the distance between said centers of curvature remains permanent. When the plate 35 tilts, they are displaced vertically but their mutual arrangement remains unchanged.

Since the centers of curvature (points 47,48, 49 and 50) of the objective mirrors 39,40,41 and 42 are spaced apart vertically with a certain displacement, a double superposition of images is produced in the matrix 46 as has been described above, but the arragement principle remains unchanged.

The number of passes of the radiation flux 1 in the system comprising four objective mirrors 39,40,41 and 42 can be obtained from the relation:

$$N=(4n-2)(m-1).$$

Overlapping of images in the matrix 46 is produced when m=4 and n=2.

In accordance with the invention, this matrix system can practically double the number of passes of the flux 1 without resorting to larger field mirrors 24 and 25.

A multiple pass optical matrix system of FIGS. 1, 4 and 8 operates as follows.

The radiation flux 1, as described above, falls at first on the objective mirror 57. The objective mirrors 57 and 58 produce two rows of images on the field mirror 24. The flux 1 reflected from the field mirror 25 falls on the objective mirror 60 which brings it back with a vertical displacement. A next pair of image raws is formed then and so on, until the last image leaves the system.

Figure 9:
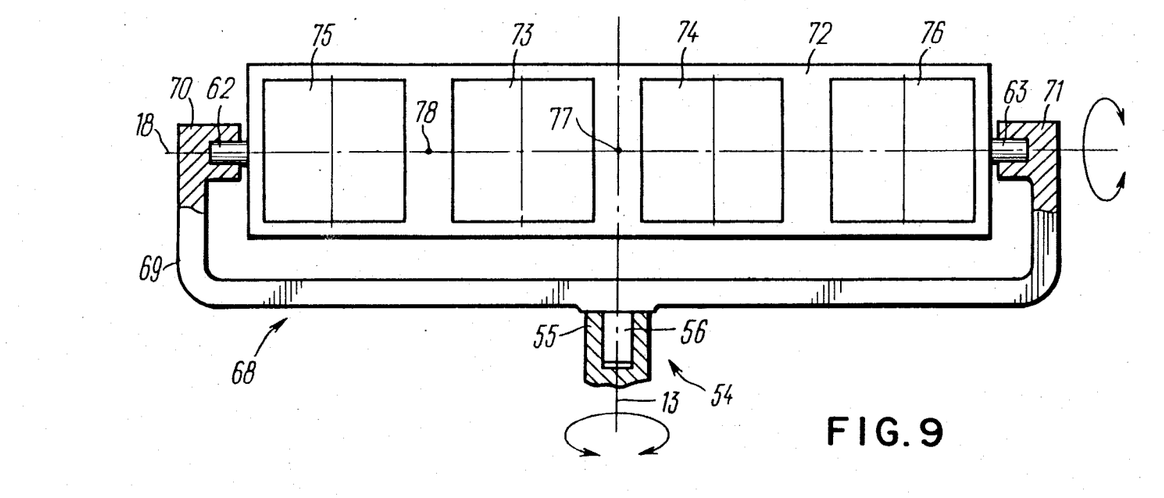
FIG. 9 shows a schematic view of a mount and four square objective mirrors arranged in a row, according to the invention.

A multiple pass optical matrix system of FIGS. 1, 7 and 9 operates as follows.

The radiation flux 1, as described above, at first comes to the objective mirror 73. The objective mirrors 73 and 74 produce two rows of images on the field mirror 24. The flux 1 is reflected from the field mirror 25 and is directed to the objective mirrors 75 and 76 which produce the next pair of image rows and so on, until the last image leaves the system.

According to the invention the objective mirrors 60,57 and 58 (FIG. 8) and objective mirrors 75,73,74 and 76 (FIG. 9) are arranged in a line and the system is easy and convenient to arrange.

The system according to the invention is simple and, consequently, reliable.

One more important feature of the invention consists in the reproducibility of the system and a very low level of aberration distortions.

INDUSTRIAL APPLICABILITY

This invention can be used to determine the atmosphere composition including microconcentrations and pollutants.

Another application of the present invention consists in studying the air transparency on open routes which can be many kilometers long.

This invention can be an important tool for high and superhigh resolution spectroscopy.

This invention can also be used as a noise-free variable optical delay line for resolution of very fast elementary processes, for calibration and synchronization of high-speed recording devices for investigating transient processes.

This invention can be successfully used in space explorations for interpretation of the atmosphere spectra of distant planets.

We claim:

1. A multiple pass optical matrix system wherein a radiation flux from an illuminating source passes through an entrance opening of a housing to one of two rigidly secured together main objective mirrors having equal radii of curvature and mechanically connected to a mount, the mount being attached to a means for rotating the main objective mirrors about an axis perpendicular to the rows of an image matrix, the radiation flux then passes to a main field mirror having a radius of curvature equal to the radii of curvature of main objective mirrors and being arranged along the longitudinal axis of the system at a distance equal to the radius of curvature of the main objective mirrors, the main field mirror directs the radiation flux to another main objective mirror, and the radiation flux is reflected therefrom to the main field mirror, and from there to the first objective mirror, and, in the last pass, leaves the system through an exit opening of the housing, wherein the improvement comprises an additional objective mirror having the same radius of curvature and mechanically connected to the mount; a means for rotating said additional objective mirror about an axis parallel to the row of the image matrix, said rotating means connected with the mount; and an auxiliary field mirror having the same radius of curvature and placed next to the main field mirror.

2. A system according to claim 1, wherein the mount is made up of two parts, one part carries the two main objective mirrors and is connected with the means for rotating the objective mirrors about an axis parallel to the row of image matrix and a second part of the mount carries the additional objective mirror.

3. A system according to claim 1, wherein the system further comprises an additional objective mirror having the same radius of curvature, mechanically connected to the mount and rigidly secured to the additional objective mirror, a center of curvature of the main field mirror being situated in a center of symmetry of the main and additional objective mirrors and a center of curvature of the auxiliary field mirror is located in a center of symmetry between the first main objective mirror and the respective additional objective mirror.

4. A system according to claim 3, wherein the mount is made as a plate and the main and additional objective mirrors are installed upon the plate.

* * * * *